(12) United States Patent  
Shapiro (10) Patent No.: US 7,909,758 B2  
(45) Date of Patent: Mar. 22, 2011

(54) APPARATUS FOR OROTRACHEAL INTUBATION

(76) Inventor: Leon Shapiro, Tenafly, NJ (US)

( * ) Notice: Subject to any disclaimer, the term of this patent is extended or adjusted under 35 U.S.C. 154(b) by 1175 days.

(21) Appl. No.: 11/590,937

(22) Filed: Oct. 31, 2006

(65) Prior Publication Data

US 2008/0103364 A1 May 1, 2008

(51) Int. Cl.  
*A61B 1/267* (2006.01)

(52) U.S. Cl. ........................................ 600/190

(58) Field of Classification Search .......... 600/185, 600/190, 191, 194, 196, 197, 199, 208, 210, 600/212, 213, 215, 226, 237; 128/200.26  
See application file for complete search history.

(56) References Cited

U.S. PATENT DOCUMENTS

| 4,295,465 | A | * | 10/1981 | Racz et al. | 600/192 |
| 4,437,458 | A | * | 3/1984 | Upsher | 600/193 |
| 5,888,195 | A | | 3/1999 | Schneider | |
| 2005/0090712 | A1 | | 4/2005 | Cubb | |

OTHER PUBLICATIONS

International Preliminary Report on Patentability dated May 5, 2009, including Written Opinion, from the International Bureau of WIPO.

* cited by examiner

*Primary Examiner* — Eduardo C Robert  
*Assistant Examiner* — David Comstock  
(74) *Attorney, Agent, or Firm* — Gary J. Gershik; Cooper & Dunham LLP (57) ABSTRACT

This invention provides a laryngoscope blade, wherein the blade comprises a tube having an opening along one side. This invention further provides a laryngoscope blade comprising at its front portion a first surface for lifting the epiglottis of a patient and a second surface for fixing the portion of the posterior part of the vocal cords of the patient.

19 Claims, 10 Drawing Sheets

APPARATUS FOR OROTRACHEAL INTUBATION

BACKGROUND

This invention relates generally to the field of tracheal intubation. More, particularly, this invention relates to an apparatus that allows for improved orotracheal intubation of patients.

Tracheal intubation is placing a tube into the trachea. The most common tracheal intubation is orotracheal intubation where an endotracheal tube is passed through the mouth, through the larynx, and into the trachea.

Tracheal intubation is performed in various medical conditions. One example is a comatose or intoxicated patient who is unable to protect their airways. In such patients, the throat muscles may lose their tone so that the upper airways obstruct or collapse and air can not easily enter into the lungs. Furthermore, protective airway reflexes such as coughing and swallowing, which serve to protect the airways against aspiration of secretions and foreign bodies, may be absent. With tracheal intubation, airway patency is restored and the lower airways can be protected from aspiration. Another example is a patient undergoing general anesthesia. In anesthetized patients, spontaneous respiration may be decreased or absent due to the effect of anesthetics, opiods or muscle relaxants. To enable mechanical ventilation, an endotracheal tube is often used, although there are alternative devices such as face masks or laryngeal mask airways. Other conditions wherein orotracheal intubations may be performed are during diagnostic manipulation of the airways, such as bronchoscopy, or endoscopic operative procedures to the airways, such as laser therapy or stenting of the bronchi. Oratracheal intubation are also performed during intensive care for patients who require respiratory support, and emergency medicine, particularly for cardiopulmonary resuscitation.

Tracheal intubation is usually performed by direct laryngoscopy (conventional technique), in which a laryngoscope is used to obtain a view of the vocal cords. A tube is then inserted under direct vision through the vocal cords. This technique can usually only be employed if the patient is comatose (unconscious), under general anesthesia, or has received local or topical anesthesia to the upper airway structures (e.g., using a local anesthetic drug such as lidocaine).

There are many types of laryngoscopes. The main categories are those for adult use and those for child use. The blade may be curved, e.g., the Macintosh; straight, e.g., the Miller blade; at a 120 degree angle, as in the polio blade; or with a hinged blade tip seen in the McCoy laryngoscope, with is commonly used in managing difficult intubations. The handle may be short to allow use when there is limited space, commonly seen during a rapid sequence induction of an obese individual where there is less room for both cricoid pressure application and performing laryngoscopy. The fibreoptic intubating laryngoscope is also used for intubation (its other uses including examination of the airway and bronchial tree). Fiberoptics are used when intubation is required in the presence of upper airway obstruction, e.g., oral abscess, tumor, angioedema, or limited neck movement. In these circumstances, the airways are carefully anesthetised with local anaesthetic and vasoconstrictor drugs before performing awake intubation.

Figure 1A:
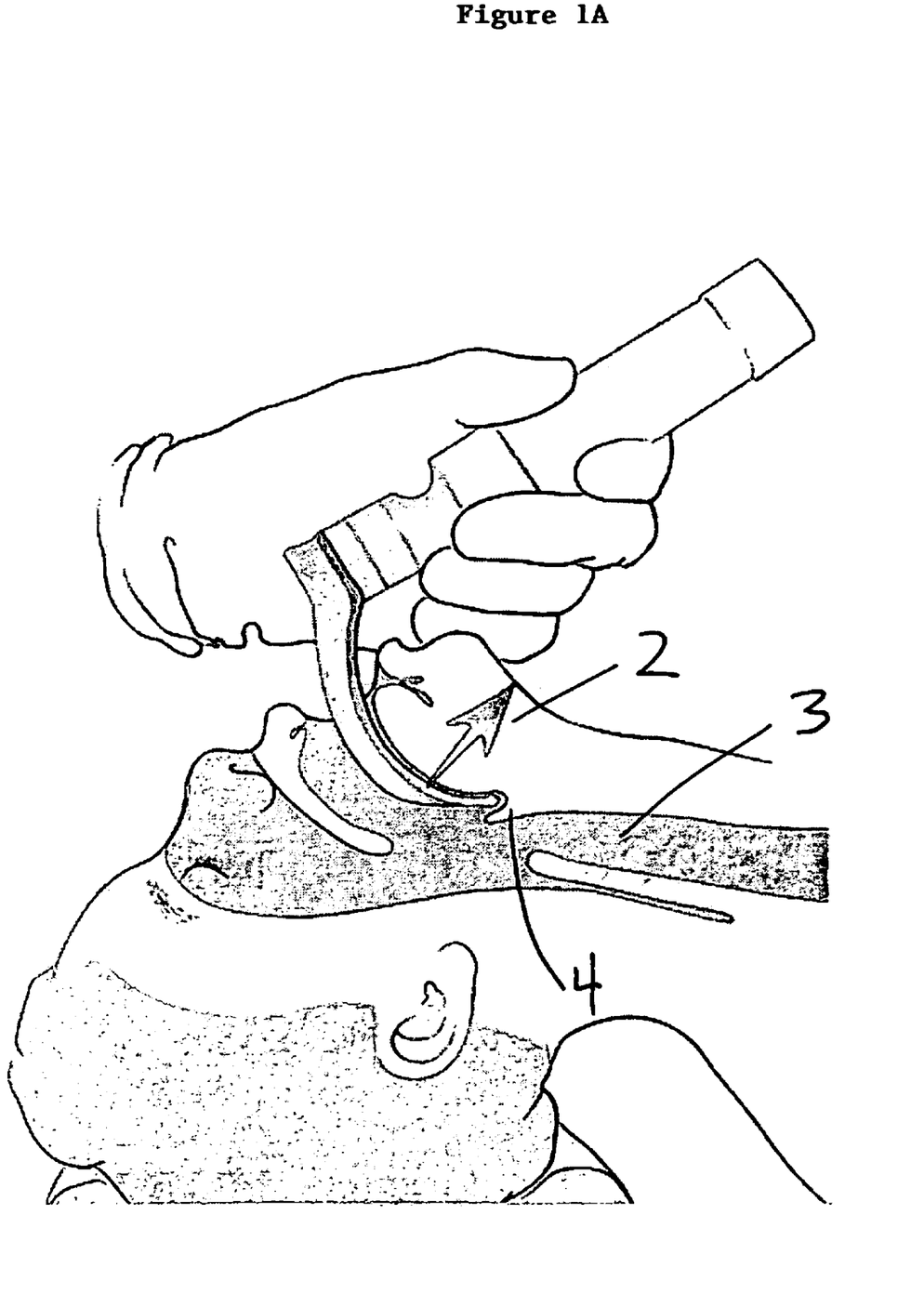
FIGS. 1A and 1B illustrate the use of a traditional laryngoscope for inserting a endotracheal tube into a subject. 1 shows the insertion of the blade into the mouth of the subject. 2 shows the direction of movement of the blade to lift the epiglottis. 3 shows the subject's larynx. 4 shows the epiglottis.
Figure 1B:
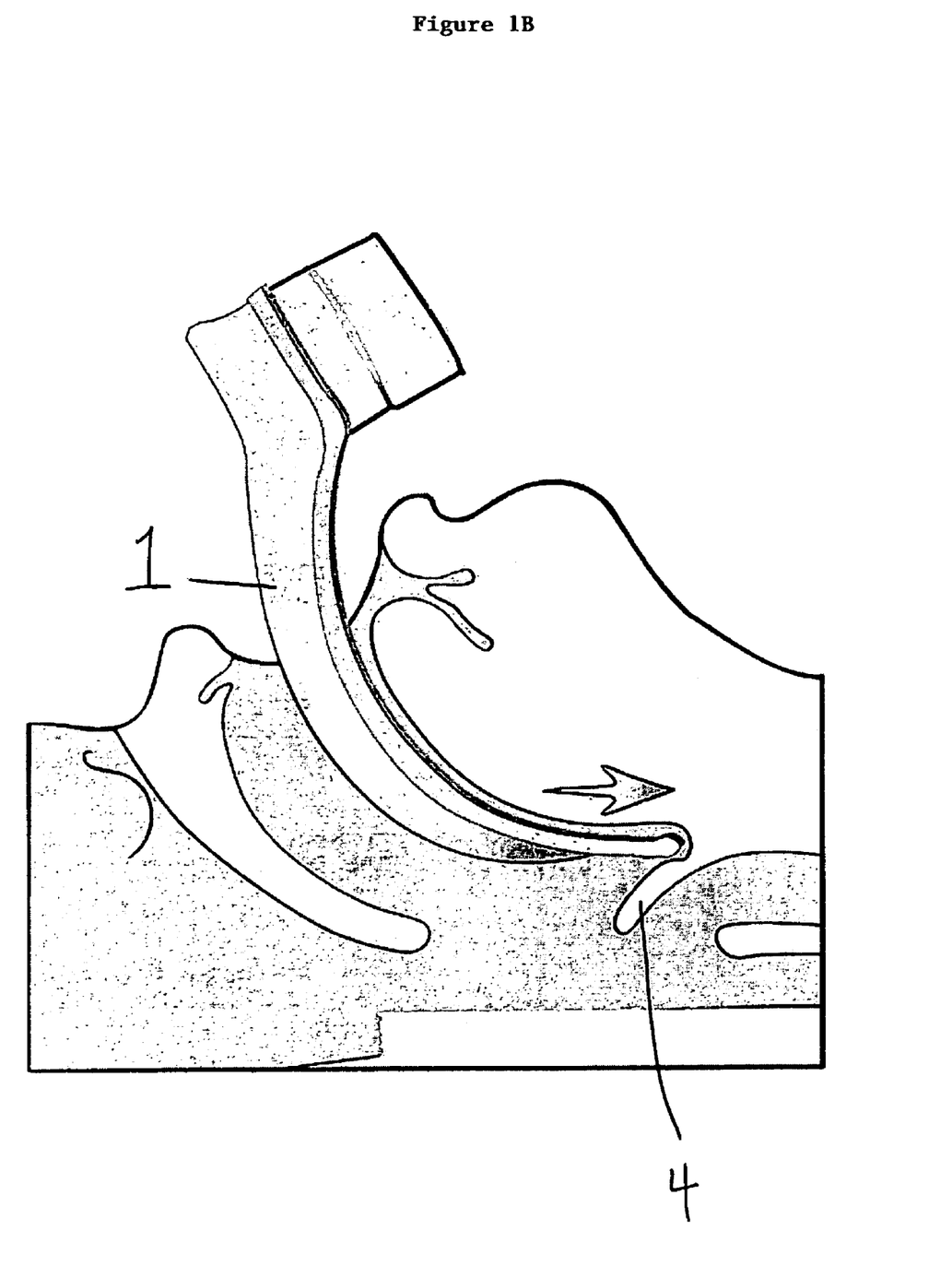

In the typical orotracheal intubation procedure (FIGS. 1A and 1B), the blade is inserted into the right corner of the patient's mouth 1. If a curved Macintosh blade is used, the flange will push the tongue to the left side of the oropharynx. After visualization of the arytenoids, the epiglottis 4 is directly lifted with the straight blade or indirectly lifted with the curved blade. The larynx 3 is then exposed by pulling the handle in the direction that it points, i.e., 90° to the blade 2. In normal patients, the vocal cords should then come into view. The tube is then advanced until the cuff disappears below the vocal cords. Correct tube placement is about 2 cm above the carina. The cuff is then inflated, an oropharyngeal airway or bite block is inserted and auscultated to verify bilateral lung expansion.

Most intubations are uncomplicated and straightforward. In patients with known intubation difficulties, measures can be taken prior to the intubation procedure to mitigate such difficulties. However, certain unforeseen circumstances can arise which can make an airway difficult to intubate, e.g., placement of vocal cords in the patient's voice box. Currently, none of the blades on the market provides a good view of the vocal cords if they are located in the vocal box more anterior relative to normal vocal cords. In such patients, using a conventional blade would cause the tube to slip into the esophagus, and the cords, which serve as an anatomical mark for proper placement of the endotracheal tube, will be out of view, i.e., located anterior to the tip of the blade. With a tube-shaped blade, the tubular shape of the blade will slide between the vocal cords, thus preventing the cords from being lifted anteriorly, as with a conventional blade, and making placement of the endotracheal tube easier or possible.

The present invention is an apparatus intended to improve the ease of intubating a patient and help overcome the problems that currently create difficulties for orotracheal intubation via traditional laryngoscope blades.

SUMMARY OF THE INVENTION

It is the object of the invention to provide a laryngoscope blade, wherein the blade comprises a tube having an opening along one side.

Another object of the invention is to provide a laryngoscope blade, wherein the blade comprises at it's front portion a first surface for lifting the epiglottis of a patient and a second surface for fixing the portion of the posterior part of the vocal cords of the patient.

It is an advantage of the present invention to facilitate orotracheal intubation of a patient.

The advantages and features of the invention will become apparent to those skilled in the art upon consideration of the following description of the invention.

The features of the invention believed to be novel are set forth with particularity in the appended claims. The invention itself, however, may be best understood by reference to the following description taken in conjunction with the accompanying figures.

BRIEF DESCRIPTION OF THE FIGURES

In FIG. 2A, the tube blade is placed below the epiglottis 4 of the subject. 9 indicates the direction of movement of the blade, compressing the tongue between the blade and the hard palate. In FIG. 2B, the blade has lifted the epiglottis 4 and placed into the entrance of the trachea. Due to the hollow tube construction of the blade 6, an endotracheal tube 7 can be placed through the blade and into the trachea.

FIGS. 3A-3F show one embodiment of the claimed invention. As depicted in the figures, the claimed laryngoscope blade comprises a tube having an opening along the full length of its one side 5. The opening may be 20-50% of the circumference of the tube. Preferably the opening is approximately 25-30% of the circumference of the tube. In this embodiment, a smaller tube 8 is shown inside the blade for which a fiber optic wand can be inserted.

DETAILED DESCRIPTION OF THE INVENTION

While this invention is susceptible of embodiment in many different forms, there is shown in the Figures and will herein be described in detail specific embodiments, with the understanding that the present disclosure is to be considered as an example of the principles of the invention and not intended to limit the invention to the specific embodiments shown and described.

This invention provides a laryngoscope blade for orotracheal intubation of a subject, wherein the blade comprises a tube having an opening along one side.

Figure 2A:
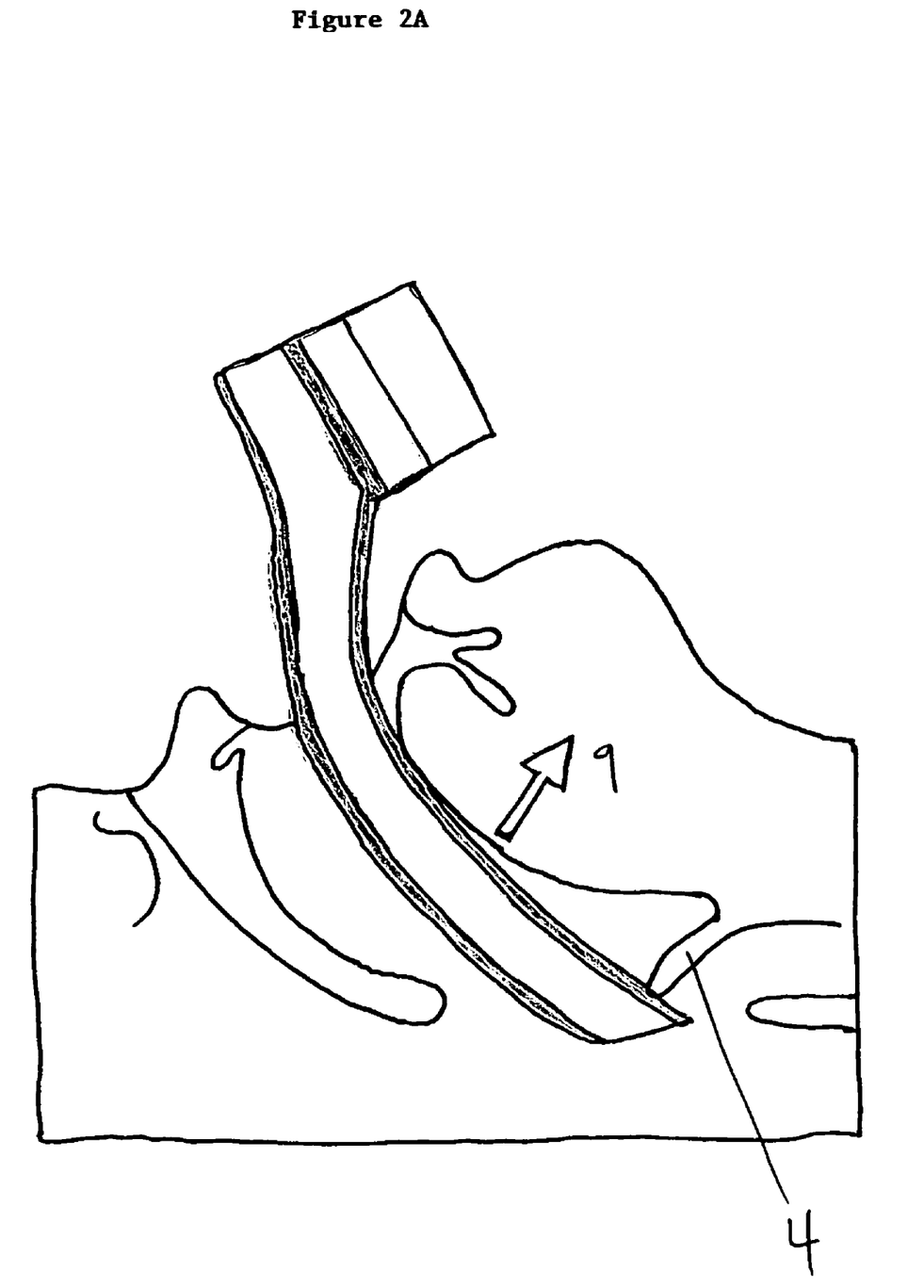
FIGS. 2A and 2B illustrate the use of one embodiment of the claimed invention for inserting an endotracheal tube into a subject.
Figure 2B:
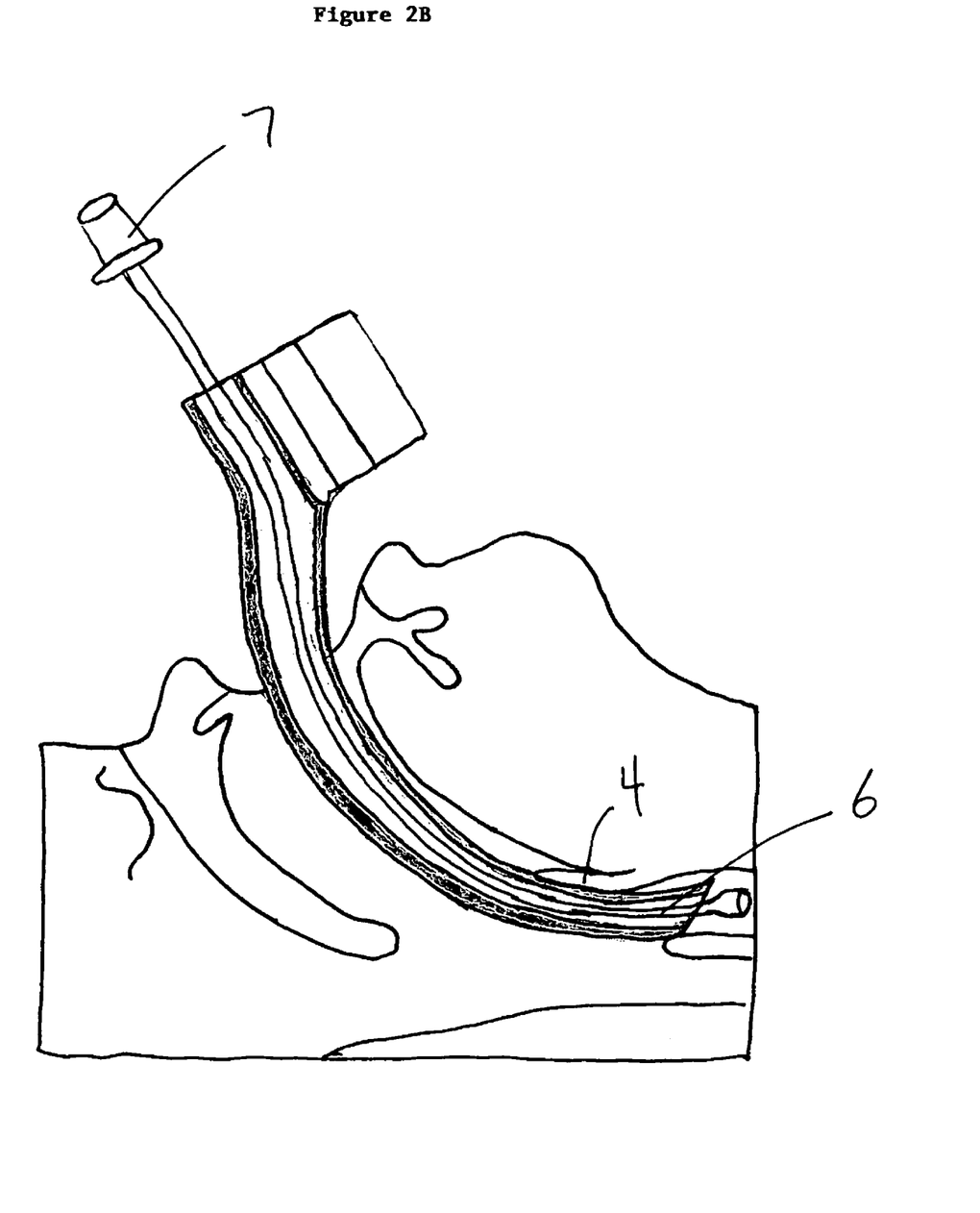
Figure 3A:
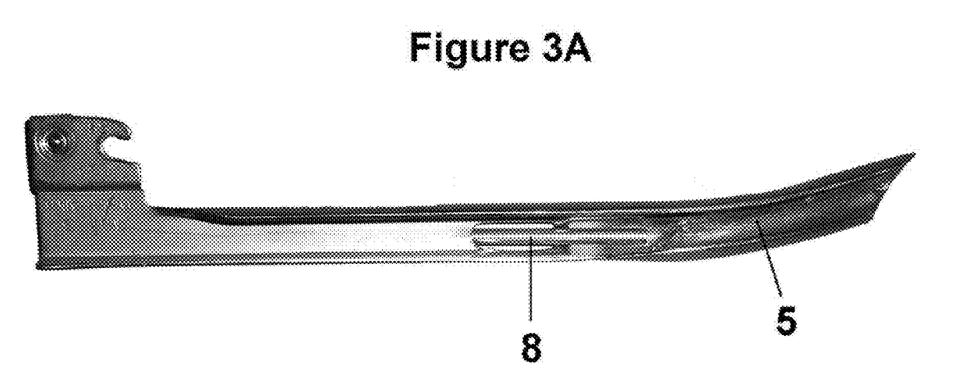
Figure 3B:
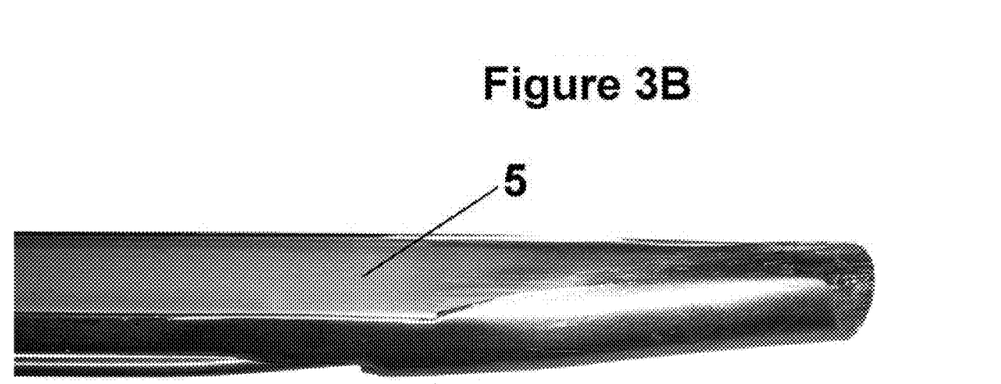
Figure 3C:
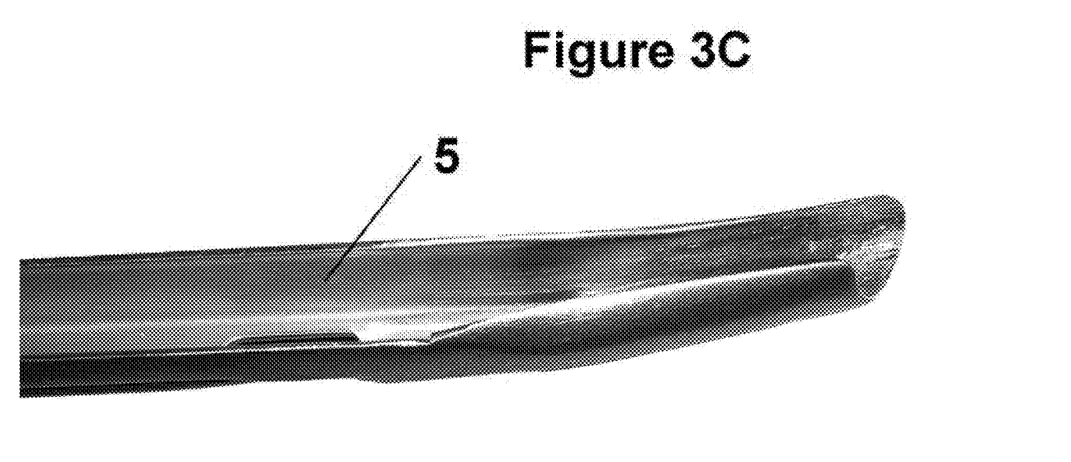
Figure 3D:
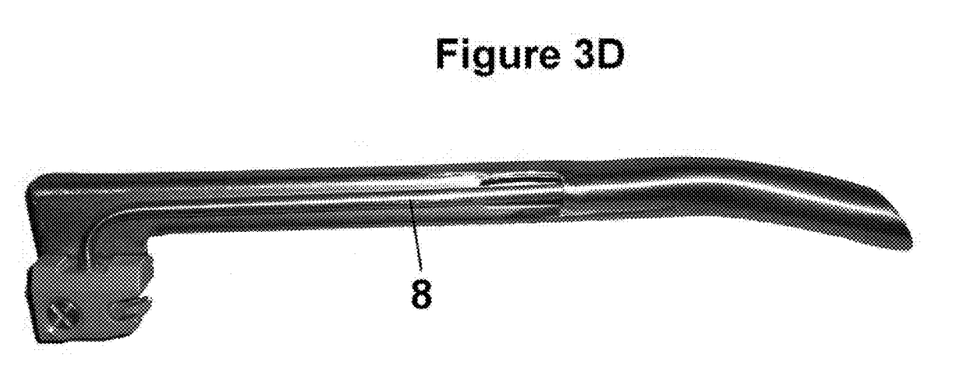
Figure 3E:
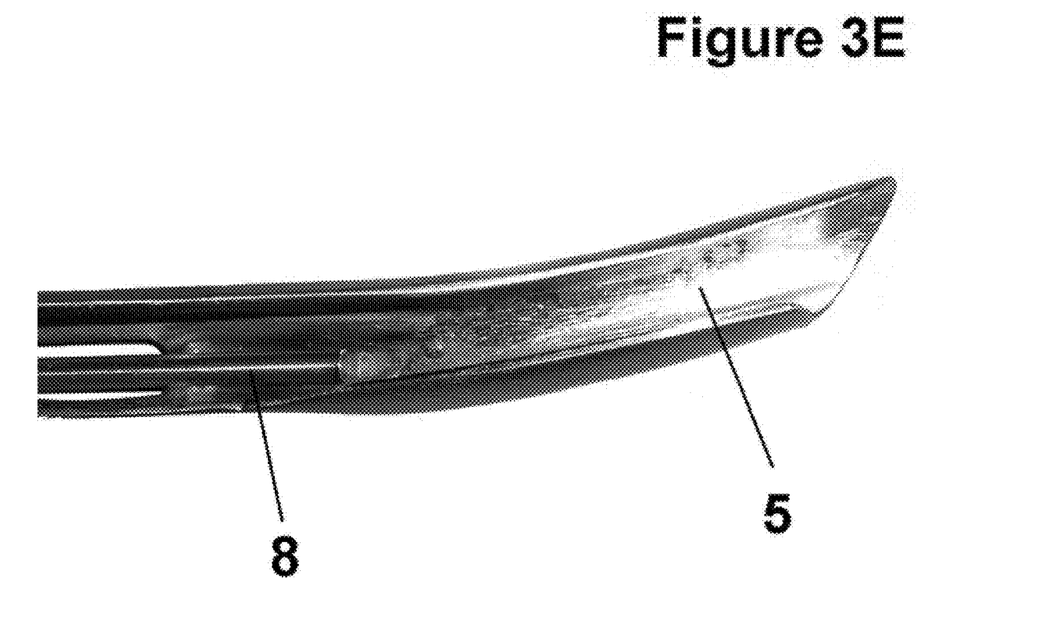
Figure 3F:
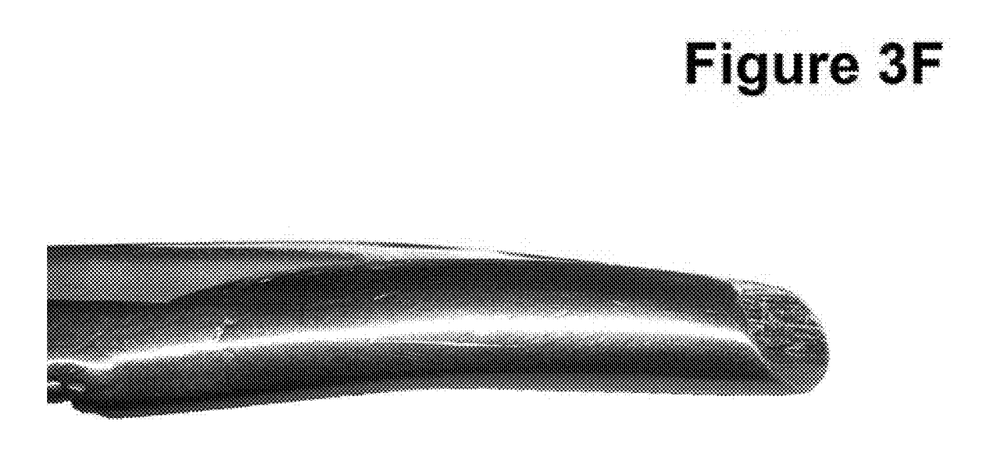

In one embodiment, the laryngoscope blade has the shape of an incomplete tube (FIGS. 3A-3F). In another embodiment, 20-50%, preferably approximately a quarter to a third of the tube wall is absent, leaving an opening running the length of one side of the blade. This opening can be on either side of the tube. This opening allows insertion of an endotracheal tube, which is then advanced through the blade and in between the vocal cords. Once the blade and endotracheal tube is properly inserted into the trachea 6 of the subject (FIGS. 2A-2B), the blade can be removed without disturbing the position of the endotracheal tube 7. Thus, the size of the opening is designed to match the diameter of the endotracheal tube so as to allow removal of the laryngoscope blade with the endotracheal tube remaining in the desired position.

Due to the tube shape of the claimed invention, the blade possesses significant advantages for intubation of a patient whose larynx is located more anterior than in normal patients. Specifically, in a patient with an anteriorly-located larynx, either no vocal cords or just the posterior cartilages of the vocal cords will fall into view upon insertion of a typical blade. Sufficient observation of the vocal cords is required for proper placement of the endotracheal tube. Currently, none of the blades on the market allow a good view of the vocal cords if they are located more anterior than normal.

The claimed laryngoscope tube will slide, and most importantly, hold fixed the posterior part of the vocal cords, therefore not allowing the vocal cords to remain in their anterior position or move to an anterior position. In other words, the larynx and the vocal cords will wrap around the tube-shaped blade rather than be pulled anteriorly as with a conventional blade. This will make the placement of the endotracheal tube easier or possible.

As used herein, the term "tube" and "tubular" are not intended to denote a perfect tube with a circular circumference. Instead, the shape can be, and preferably is, irregular but sufficiently curved to allow the operator to lift the epiglottis with one portion and hold fixed the posterior part if the vocal cords with another position, and allow for intubation of the patient.

In another embodiment of the claimed invention, a smaller tube 8 is located within the inner walls of the blade, allowing insertion of a light source. In one embodiment, the light source is a fiber optic wand. In another embodiment, the laryngoscope blade is straight. In another embodiment, the laryngoscope blade is curved. In another embodiment, the laryngoscope blade can be adjusted to varying degrees of curvature, i.e., a flexed-tip blade. In another embodiment, the end of the laryngoscope blade opposite the end to be inserted into the subject's mouth is capable of being attached and removed from a handle. In another embodiment, the handle contains a light source and/or a power source.

In one embodiment, the blade is made of stainless steel. In another embodiment, the blade is made of plastic. The blade can be either intended for multiple use or one-time use.

This invention further provides a laryngoscope blade comprising at its front portion a first surface for lifting the epiglottis of a patient and a second surface for fixing the portion of the posterior part of the vocal cords of the patient.

In one embodiment, the laryngoscope blade comprises a canal between the first and second surfaces which canal is exposed along the length of the blade. In another embodiment, the canal comprises 20% to 50% of the total tube wall. In a preferred embodiment, the canal comprises approximately a quarter to a third of the total tube wall.

In another embodiment, a light source is located within the inner walls of the blade. In another embodiment, the blade is straight. In another embodiment, the blade is curved. In another embodiment, the blade can be adjusted to varying degrees of curvature, i.e., a flexed-tip blade. In another embodiment, the end opposite the end to be inserted into the subject's mouth is capable of being attached and removed from a handle.

In one embodiment, the blade is made of stainless steel. In another embodiment, the blade is made of plastic. The blade can be either intended for multiple use or one-time use.

Accordingly, it is intended that the present invention embrace all such alternatives, modifications and variations that fall within the scope of the appended claims.

I claim:

1. A laryngoscope blade for attachment to a handle such that the handle would extend from a first side of the laryngoscope blade, wherein the blade comprises a tubular portion having an opening along the full length of one lateral side, wherein the one lateral side is positioned approximately ninety degrees from the first side, and wherein the blade is curved, the curvature being in a direction generally toward the first side and not generally toward the one lateral side or the side opposite the one lateral side.

2. The laryngoscope blade of claim 1, wherein the opening comprises 20% to 50% of the total tube wall.

3. The laryngoscope blade of claim 2, wherein the opening comprises approximately a quarter to a third of the total tube wall.

4. The laryngoscope blade of claim 1, wherein a light source is located within the inner walls of the blade.

5. The laryngoscope blade of claim 1, wherein the blade can be adjusted to varying degrees of curvature.

6. The laryngoscope blade of claim 1, wherein the end opposite the end to be inserted into the subject's mouth is capable of being attached and removed from a handle.

7. The laryngoscope blade of claim 1, wherein the laryngoscope blade is made of stainless steel.

8. The laryngoscope blade of claim 1, wherein the laryngoscope blade is made of plastic.

9. The laryngoscope blade of claim 1, wherein a first surface at the first side extends distally relative to a second surface at a side opposite the first side sufficiently for insertion of the blade, including the second surface, into the larynx while the first surface is lifting the epiglottis of the patient.

10. A laryngoscope blade for attachment to a handle such that the handle would extend from a first side of the laryngoscope blade comprising at its front portion a first surface for lifting the epiglottis of a patient and a second surface extending circumferentially relative to the first surface sufficiently for fixing the posterior part of the vocal cords of the patient while the first surface is lifting the epiglottis of the patient, and further comprising a canal between the first and second surfaces which canal is exposed along the length of one lateral side of the blade, wherein the one lateral side is positioned approximately ninety degrees from the first side, and wherein the blade is curved, the curvature being in a direction generally toward the first surface and not generally toward the one lateral side or the side opposite the one lateral side.

11. The laryngoscope blade of claim 10, wherein the canal comprises 20% to 50% of the total tube wall.

12. The laryngoscope blade of claim 11, wherein the canal comprises approximately a quarter to a third of the total tube wall.

13. The laryngoscope blade of claim 10, wherein a light source is located within the inner walls of the blade.

14. The laryngoscope blade of claim 10, wherein the blade can be adjusted to varying degrees of curvature.

15. The laryngoscope blade of claim 10, wherein the end opposite the end to be inserted into the subject's mouth is capable of being attached and removed from a handle.

16. The laryngoscope blade of claim 10, wherein the laryngoscope blade is made of stainless steel.

17. The laryngoscope blade of claim 10, wherein the laryngoscope blade is made of plastic.

18. The laryngoscope blade of claim 10, wherein the first surface extends distally relative to the second surface sufficiently for insertion of the blade, including the second surface, into the larynx while the first surface is lifting the epiglottis of the patient.

19. The laryngoscope blade of claim 10, wherein the second surface extends circumferentially relative to the first surface sufficiently to be positioned in close proximity to the posterior point of vocal cords attachment while the first surface is positioned in close proximity to the anterior point of vocal cords attachment.

* * * * *